United States Patent
Kim et al.

(10) Patent No.: US 10,013,757 B2
(45) Date of Patent: Jul. 3, 2018

(54) CLASSIFICATION APPARATUS FOR PATHOLOGIC DIAGNOSIS OF MEDICAL IMAGE, AND PATHOLOGIC DIAGNOSIS SYSTEM USING THE SAME

(71) Applicant: LUNIT INC., Seoul (KR)

(72) Inventors: Hyo-eun Kim, Seoul (KR); Sang-heum Hwang, Seoul (KR); Seung-wook Paek, Seoul (KR); Jung-in Lee, Seoul (KR); Min-hong Jang, Seoul (KR); Dong-geun Yoo, Daejeon (KR); Kyung-hyun Paeng, Busan (KR); Sung-gyun Park, Gyeonggi-do (KR)

(73) Assignee: LUNIT INC., Seoul (KR)

( * ) Notice: Subject to any disclaimer, the term of this patent is extended or adjusted under 35 U.S.C. 154(b) by 16 days.

(21) Appl. No.: 15/113,644

(22) PCT Filed: Sep. 8, 2015

(86) PCT No.: PCT/KR2015/009447
§ 371 (c)(1),
(2) Date: Jul. 22, 2016

(87) PCT Pub. No.: WO2017/022882
PCT Pub. Date: Feb. 9, 2017

(65) Prior Publication Data
US 2017/0236271 A1 Aug. 17, 2017

(30) Foreign Application Priority Data

Aug. 6, 2015 (KR) .................. 10-2015-0111277

(51) Int. Cl.
*G06K 9/00* (2006.01)
*G06T 7/00* (2017.01)
(Continued)

(52) U.S. Cl.
CPC ...... *G06T 7/0012* (2013.01); *G06F 17/30244* (2013.01); *G06F 19/321* (2013.01);
(Continued)

(58) Field of Classification Search
None
See application file for complete search history.

(56) References Cited

U.S. PATENT DOCUMENTS

| 6,898,528 B2 * | 5/2005 | Zorka | G08G 1/163 180/271 |
| 7,421,415 B2 * | 9/2008 | Dong | G06K 9/6256 706/12 |

(Continued)

FOREIGN PATENT DOCUMENTS

| KR | 10-2013-0012297 A | 2/2013 |
| KR | 10-2013-0079863 A | 7/2013 |

(Continued)

*Primary Examiner* — Hadi Akhavannik
(74) *Attorney, Agent, or Firm* — Rabin & Berdo, P.C.

(57) ABSTRACT

The present invention relates to a classification apparatus for pathologic diagnosis of a medical image and a pathologic diagnosis system using the same. According to the present invention, there is provided a classification apparatus for pathologic diagnosis of a medical image, including: a feature extraction unit configured to extract feature data for an input image using a feature extraction variable; a feature vector transformation unit configured to transform the extracted feature data into a feature vector using a vector transform variable; and a vector classification unit configured to classify the feature vector using a classification variable, and to output the results of the classification of pathologic diagnosis for the input image; wherein the feature extraction unit, the feature vector transformation unit and the vector classification unit are trained based on a first tagged image, a second tagged image, and an image having no tag information.

8 Claims, 8 Drawing Sheets

(51) Int. Cl.
*G06F 19/00* (2018.01)
*G06F 17/30* (2006.01)
*G06N 99/00* (2010.01)
*G06K 9/48* (2006.01)
*G06K 9/62* (2006.01)
*G06K 9/66* (2006.01)
*G06T 7/11* (2017.01)
*A61B 8/08* (2006.01)
*G16H 50/20* (2018.01)

(52) U.S. Cl.
CPC .......... *G06K 9/481* (2013.01); *G06K 9/6267* (2013.01); *G06K 9/66* (2013.01); *G06N 99/005* (2013.01); *G06T 7/11* (2017.01); *A61B 8/0825* (2013.01); *G06F 19/345* (2013.01); *G06K 2209/05* (2013.01); *G06T 2207/20021* (2013.01); *G06T 2207/20081* (2013.01); *G06T 2207/30096* (2013.01); *G16H 50/20* (2018.01)

(56) References Cited

U.S. PATENT DOCUMENTS

| | | | |
|---|---|---|---|
| 7,492,937 B2* | 2/2009 | Ramsay | G06K 9/3241 378/57 |
| 7,542,947 B2* | 6/2009 | Guyon | G06F 19/24 706/12 |
| 2006/0224539 A1* | 10/2006 | Zhang | G06K 9/623 706/20 |
| 2013/0030278 A1 | 1/2013 | Seong et al. | |
| 2013/0170718 A1 | 7/2013 | Ryu et al. | |
| 2014/0037159 A1 | 2/2014 | Cho et al. | |
| 2014/0101080 A1 | 4/2014 | Lee et al. | |
| 2014/0142413 A1 | 5/2014 | Chang et al. | |

FOREIGN PATENT DOCUMENTS

| | | |
|---|---|---|
| KR | 10-2014-0018748 A | 2/2014 |
| KR | 10-2014-0042531 A | 4/2014 |
| KR | 10-2014-0063288 A | 5/2014 |

* cited by examiner

CLASSIFICATION APPARATUS FOR PATHOLOGIC DIAGNOSIS OF MEDICAL IMAGE, AND PATHOLOGIC DIAGNOSIS SYSTEM USING THE SAME

TECHNICAL FIELD

The present invention relates to a classification apparatus for pathologic diagnosis of a medical image and a pathologic diagnosis system using the classification apparatus for pathologic diagnosis of a medical image, and more particularly to an apparatus and system that can efficiently classify a medical image through training based on machine learning and then can perform pathologic diagnosis.

BACKGROUND ART

Pathology is a medical field in which whether an abnormality is present is determined by examining a tissue sample with the naked eye or a microscope and then analyzing the results of the examination. For example, in order to diagnose cancer, a pathologist makes a diagnosis of cancer by examining a tissue sample of a corresponding suspected tissue via a microscope and then determining whether a cancer cell is present. This is referred to as pathologic diagnosis. This pathologic diagnosis is the procedure of confirming a diagnosis of a suspected lesion of a patient, and may be viewed as the final step of diagnosis.

In order to automatically perform pathologic diagnosis using equipment such as a computer or the like, there are required images and pathologic diagnosis data in which existing images, used to be compared with an input query image and to perform analysis, and corresponding results of pathologic diagnosis have been organized into a database.

The database to be compared and analyzed needs to store normal and abnormal medical images, and the medical images each having information about the presence or absence of a lesion, the result of pathologic diagnosis of the lesion, and the location of the corresponding lesion. And an input query image are compared with the medical images stored in the database and analyzed. The information about the presence or absence of a lesion, the result of pathologic diagnosis of the lesion, and the location of the lesion are referred to as tag information. The database has higher reliability in proportion to the number of medical images including such tag information. In particular, if information optimized for prediction is always maintained by training based on a massive amount of images having such tag information using a technology such as machine learning, more accurate results can be predicted.

However, in a medical imaging field, there has not been proposed a technology that can predict the result of pathologic diagnosis of a lesion by efficiently performing the analysis and diagnosis of a medical image using a learning technology such as machine learning or the like.

Furthermore, there are many cases in which various types of medical images used in existing medical institutions have not been put into databases or have not been organized. In particular, for most cases, even when an image itself is present, there is no information about the presence or absence of a lesion in the corresponding image, the result of pathologic diagnosis of the lesion, or the location of the lesion, i.e., no tag information. Furthermore, there are many cases in which even when tag information is present, the location information of a lesion is not present and tag information indicative of only the presence or absence of the lesion or the result of pathologic diagnosis of the corresponding lesion is present. Accordingly, there are many difficulties in constructing a reliable database.

DISCLOSURE

Technical Problem

The present invention is intended to overcome the above-described problems of the conventional art, and an object of the present invention is to provide a classification apparatus for pathologic diagnosis of a medical image that can efficiently be trained based on machine learning in order to perform the analysis of a medical image.

Another object of the present invention is to provide a classification apparatus for pathologic diagnosis of a medical image that can improve learning efficiency and reliability by using both a smaller amount of location information of a lesion and a larger amount of information about the presence or absence of the lesion and the pathologic diagnosis result of the lesion.

A further object of the present invention is to provide a pathologic diagnosis system that can perform pathologic diagnosis using the above-described classification apparatus for pathologic diagnosis of a medical image.

Technical Solution

According to the present invention, there is provided a classification apparatus for pathologic diagnosis of a medical image, including: a feature extraction unit configured to extract feature data for an input image using a feature extraction variable; a feature vector transformation unit configured to transform the extracted feature data into a feature vector using a vector transform variable; and a vector classification unit configured to classify the feature vector using a classification variable, and to output results of the classification of pathologic diagnosis for the input image; wherein the feature extraction unit, the feature vector transformation unit and the vector classification unit are trained based on a first tagged image having a first tag indicative of presence or absence of a lesion and pathologic diagnosis information, a second tagged image having a first tag as well as a second tag indicative of location information of the lesion, and an image having no tag.

It is preferred that the feature extraction variable is trained based on the second tagged image; the transform variable is trained based on at least one of the first tagged image, the second tagged image and the image having no tag; and the classification variable is trained based on at least one of the first tagged image and the second tagged image.

The training module may configured to generate patch images that are partial images of the input image input to the feature extraction unit, and separate the patch images into data for training and data for verification; and to adjust the feature extraction variable of the feature extraction unit by repeating a process of adjusting the feature extraction variable and the classification variable so that a cost function is minimized for the data for training until a time at which the cost function for the data for verification is minimized.

The training module may configured to set initial values of the feature extraction variable and the classification variable; and to adjust the feature extraction variable and the classification variable by repeating i) a first process of calculating feature data and results of the classification based on a current feature extraction variable and a current classification variable, ii) a second process of calculating costs for the feature extraction variable and the classification variable using cost functions, and iii) a third process of calculating variations of the feature extraction variable and the classification variable so that the costs are minimized, calculating differences with respect to an existing feature extraction variable and an existing classification variable, and updating the feature extraction variable and the classification variable.

The training module may configured to extract a plurality of pieces of feature data by inputting the plurality of patch images for the input image to the feature extraction unit, and to estimate the transform variable adapted to transform the feature data into a fixed length feature vector, thereby enabling the feature vector transformation unit to be trained.

The training module may configured to generate patch images that are partial images of the input image, and separates the patch images into data for learning and data for verification; and to adjust the classification variable of the vector classification unit by repeating a process of adjusting the classification variable so that a cost function is minimized for the data for training until a time at which a cost function for the data for verification is minimized.

It is preferred that the training module sets an initial value of the classification variable; and adjusts the classification variable by repeating i) a first process of calculating results of the classification based on a current classification variable, ii) a second process of calculating a cost for the classification variable using a cost function, and iii) a third process of calculating a variation of the classification variable so that the cost is minimized, calculating a difference with respect to an existing classification variable, and updating the classification variable.

It is preferred that the feature extraction unit receives the plurality of patch images obtained by segmenting the input image, and extracts feature data for each of the patch images using the feature extraction variable; the feature vector transformation unit transforms the feature data for the patch images into a fixed length feature vector using the transform variable; and the vector classification unit classifies the fixed length feature vector using the classification variable, and outputs results of classification of pathologic diagnosis for the input image.

According to another aspect of the present invention, there is provided a pathologic diagnosis system, including: the above-described classification apparatus for pathologic diagnosis of a medical image; a testing module configured to output final analysis information for an input image based on results of pathologic diagnosis output for the input image by the apparatus for classification of pathologic diagnosis of a medical image; a training module configured to train the apparatus for classification of pathologic diagnosis of a medical image based on tagged images stored in a tagged image database; and a tagged image database configured to store tagged images, including first tagged images each having a first tag indicative of presence or absence of a lesion and pathologic diagnosis information, and second tagged images each having a second tag indicative of location information of a lesion as well as a first tag.

Advantageous Effects

According to the present invention, there can be provided a classification apparatus for pathologic diagnosis of a medical image that can efficiently be trained based on machine learning in order to perform the analysis of a medical image.

Furthermore, there can be provided a classification apparatus for pathologic diagnosis of a medical image that can improve learning efficiency and reliability by using both a smaller amount of location information of a lesion and a larger amount of information about the presence or absence of the lesion and the pathologic diagnosis result of the lesion.

Furthermore, there can be provided a pathologic diagnosis system that can perform pathologic diagnosis using the above-described classification apparatus for pathologic diagnosis of a medical image.

BEST MODE

Embodiments of the present invention will be described in detail below with reference to the accompanying drawings.

Figure 1:
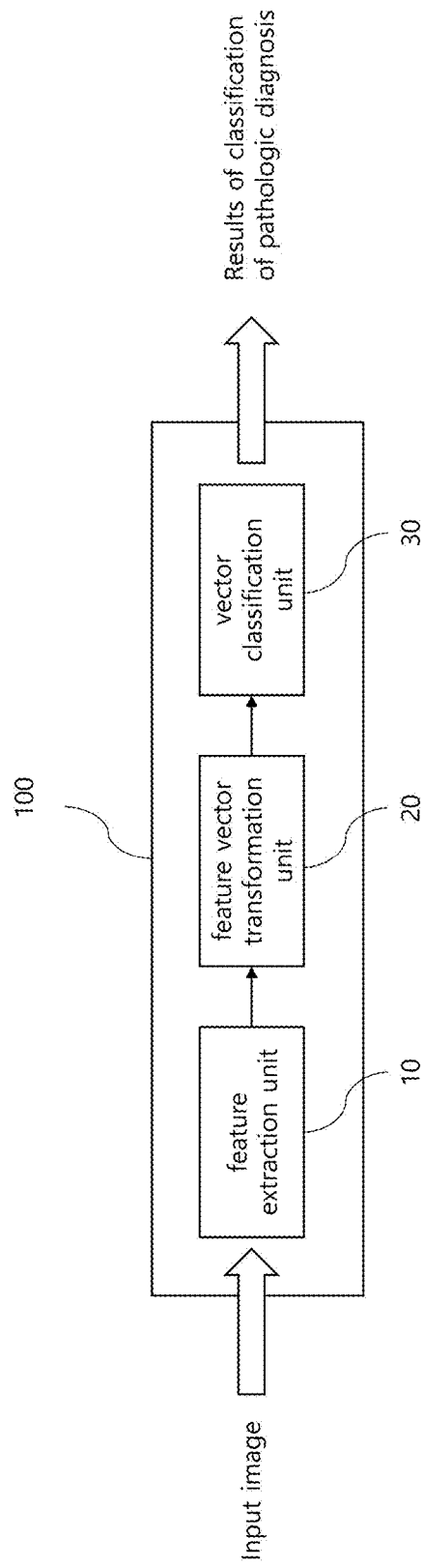
FIG. 1 is a diagram showing the configuration of a classification apparatus 100 for pathologic diagnosis of a medical image according to the present invention.

FIG. 1 is a diagram showing the configuration of a classification apparatus 100 for pathologic diagnosis of a medical image according to the present invention.

Referring to FIG. 1, the classification apparatus 100 for pathologic diagnosis of a medical image (hereinafter simply referred to as the "classifier 100") includes a feature extraction unit 10, a feature vector transformation unit 20, and a vector classification unit 30.

The feature extraction unit 10 functions to extract feature data for an input image using a feature extraction variable. The feature vector transformation unit 20 functions to transform the feature data, extracted by the feature extraction unit 10, into a feature vector using a transform variable. The vector classification unit 30 functions to classify the feature vector, obtained by the transformation of the feature vector transformation unit 20, using a classification variable and to output the results of the classification of pathologic diagnosis of the input image.

Here, the feature extraction variable refers to a variable that is used to extract a feature for an input image, and the transform variable refers to a variable that is used to transform feature data into a feature vector. Furthermore, the classification variable refers to a variable that is used to classify a feature vector.

Figure 3:
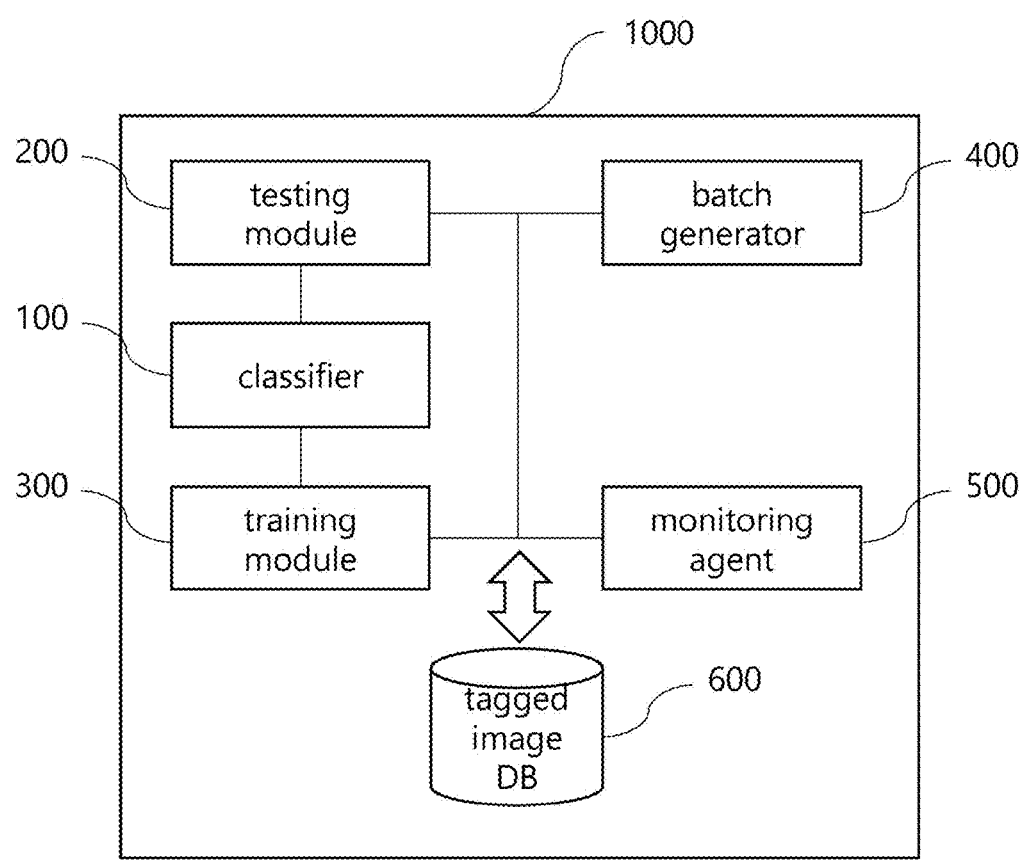
FIG. 3 is a diagram showing the overall configuration of a pathologic diagnosis system 1000 including the classifier 100 according to the present invention.

The classifier 100 is characterized by outputting the results of the classification of pathologic diagnosis of a input medical image while being trained by a training module (see FIG. 3). Here, the results of the classification of pathologic diagnosis may be output in the form of probability values.

In particular, the feature extraction unit 10, feature vector transformation unit 20 and vector classification unit 30 of the classifier 100 according to the present invention are characterized in that training (learning) is performed using a first tagged image having a first tag indicative of the presence or absence of a lesion and pathologic diagnosis information, a second tagged image having a second tag indicative of the location information of a lesion as well as a first tag, and a general medical image having no tag information.

More specifically, the present invention is characterized in that the feature extraction variable that is used in the feature extraction unit 10 is trained based on a second tagged image, the vector transform variable that is used in the feature vector transformation unit 20 is trained based on the characteristics of an input image itself exclusive of tag information and, thus, is trained based on at least any one of all types of medical images (that is, at least any one of a first tagged image, a second tagged image and an image having no tag information) regardless of the presence or absence of tag information, and the classification variable that is used in the vector classification unit 30 is trained based on at least any one of a first tagged image and a second tagged image.

Figure 2:
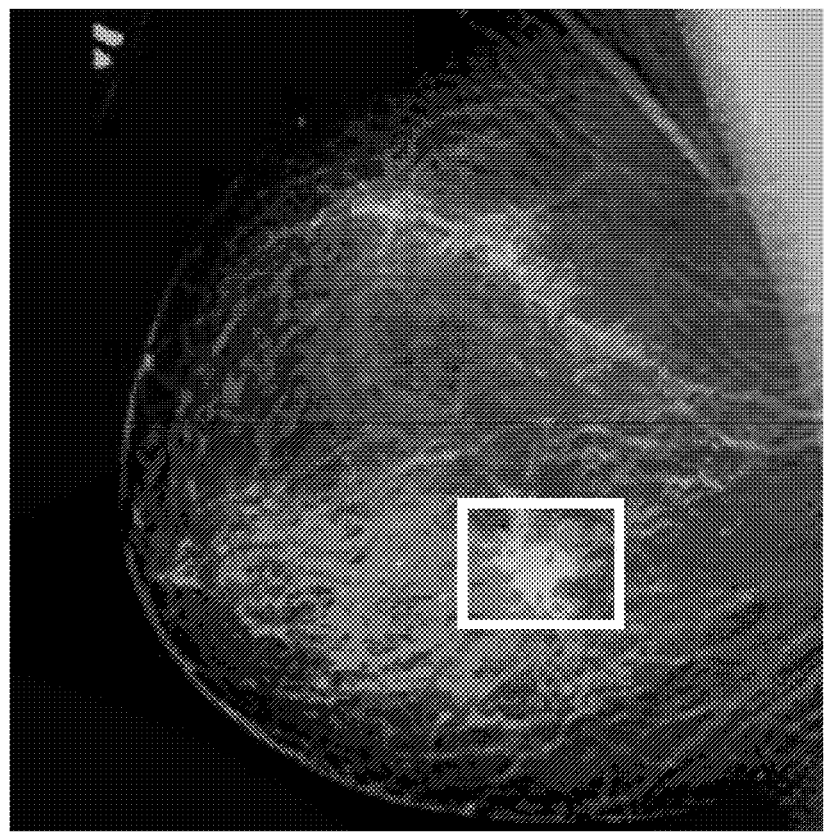
FIG. 2 is a view illustrating a tag that is used in the present invention.

FIG. 2 is a view illustrating a tag that is used in the present invention.

FIG. 2 is a mammographic X-ray image, in which a portion indicated by a while rectangle shows a cancer cell tissue (lesion). Here, when a tag for the image of FIG. 2 includes only "breast cancer," the tag is indicative of the presence or absence of a lesion and pathologic diagnosis information, and is thus referred to as a first tag. An image to which such a first tag is attached is referred to as a first tagged image.

Meanwhile, when tags for the image of FIG. 2 include "breast cancer" and "(x,y) coordinate values," this case corresponds to a case where the location information of the lesion (the coordinate values of the while rectangle in FIG. 2) as well as the presence or absence of a lesion and pathologic diagnosis information are included. Accordingly, this image has a first tag and a second tag and may be referred to as a second tagged image.

In order to achieve higher reliability when learning is performed, a larger amount of data is required. In particular, the efficiency of learning increases in proportion to the number of second tagged images each including the location information of a lesion. However, in most cases, images actually do not have tag information or are first tagged images having only information about the presence or absence of a lesion or diagnosis information, and second tagged images having second tag information which is the location information of a lesion as well as first tag information, are unusual. Accordingly, this is the main cause of a reduction in the reliability of learning.

Accordingly, the classifier 100 of the present invention is characterized by enabling training (learning) to be more efficiently and more reliably performed by appropriately using a limited number of second tagged images and relatively large amounts of first tagged images and images having no tag information for the variables at the respective steps that are used during training process.

FIG. 3 is a diagram showing the overall configuration of a pathologic diagnosis system 1000 including the classifier 100 according to the present invention.

Referring to FIG. 3, the pathologic diagnosis system 1000 (hereinafter simply referred to as the "system 1000") includes a classifier 100, a testing module 200, a training module 300, a batch generator 400, a monitoring agent 500, and a tagged image database 600.

The classifier 100 performs an operation of classifying the results of pathologic diagnosis of an input image by extracting feature data for the input image, transforming the feature data into a feature vector, and then classifying the feature vector, as described above.

The testing module 200 is a means that receives an input image, receives the results of pathologic diagnosis from the classifier 100 by way of the classification of the input image, and outputs final analysis information (the results of diagnosis) for the input image based on the results of pathologic diagnosis. Although not shown in the drawings, the testing module 200 may include a preprocessing unit that performs a preprocessing operation of structuring an input image into a form that can be used in the system 1000.

The classifier 100 outputs the results of the classification of pathologic diagnosis for the input image. The results of the classification may represent lesion presence or absence information indicative of the presence or absence of a lesion and lesion pathologic diagnosis result information in the form of probability values, or may represent lesion location information indicative of the location of the lesion as well as the above information in the form of probability values. The testing module 200 generates the final results of the analysis of the input image by receiving the results of the classification, and generating, processing and manipulating other analysis information related to the results of the classification.

In this case, the other analysis information may include comprehensive diagnosis information (information about the presence or absence of an abnormality, etc.) including the number of locations of lesions for the input image and final pathologic diagnosis results into which the number of locations of the lesions has been incorporated. Furthermore, it may be possible to represent the final pathologic diagnosis result information based on the probability values of the lesions, output by the classifier 100, in the form of probability values, and include these probability values in the other analysis information.

The training module 300 is a module that enables the classifier 100 to be trained based on tagged images stored in the tagged image database 600. The training module 300 receives batch data generated by the batch generator 400 that will be described later, and enables the classifier 100 to be trained based on the batch data. A process in which the training module 300 makes the classifier 100 be trained is described in detail with reference to FIG. 4 and its following drawings as well.

Meanwhile, the batch generator 400 is responsible for the function of generating batch data, i.e., a bundle of tagged images stored in the tagged image database 600 (including images and tag information of the corresponding images), and transmitting the batch data to the training module 300, thereby enabling the classifier 100 to be trained based on the batch data.

The monitoring agent 500 monitors the operations of the individual components of the system 1000, and controls the overall operation of these components.

The monitoring agent 500 determines the start time and end time of training and the start time and end time of re-training while monitoring the operations of the training module 300 and the classifier 100 in connection with the training module 300. The monitoring agent 500 also receives current training state information from the training module 300.

Furthermore, the monitoring agent 500 controls the operation of the batch generator 400 by transmitting and receiving a batch data generation instruction and a completion signal to and from the batch generator 400.

Furthermore, the monitoring agent 500 transmits an instruction to direct the testing module 200 to check the current performance state of the classifier 100, and receives the state information of the classifier 100 from the testing module 200.

The tagged image database 600 is a database that stores tagged images. As described above, the tagged images include first tagged images each having a first tag indicative of the presence or absence of a lesion and pathologic diagnosis information and second tagged images each having a second tag indicative of the location information of a lesion as well as a first tag.

Meanwhile, although not shown in the drawings, the system 100 may include an untagged image database that stores images having no tag information that are used during the training of classification variables.

A training process that is performed in the system 1000 configured as described above is described in detail with reference to FIG. 4 and its following drawings as well.

Figure 4:
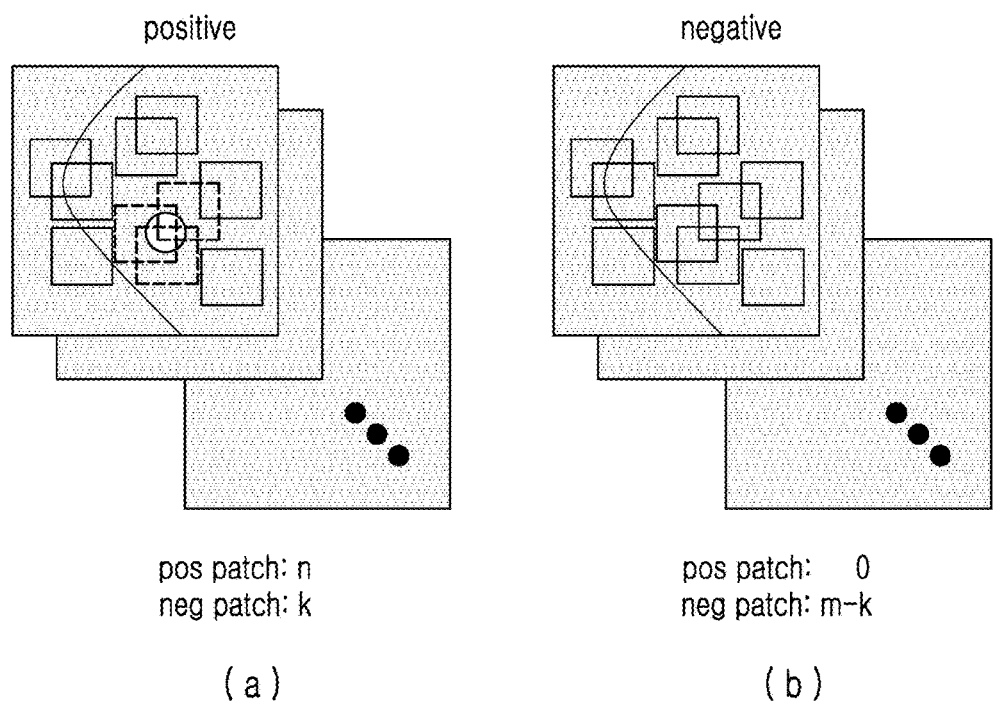
FIG. 4 is a diagram illustrating a process in which the feature extraction unit 10 of the classifier 100 is trained by means of the training module 300.

FIG. 4 is a diagram illustrating a process in which the feature extraction unit 10 of the classifier 100 learns feature extraction variables by means of the training module 300.

FIG. 4 shows batch data, i.e., a bundle of input images that are input to the feature extraction unit 10. As described above, the batch data is generated by the batch generator 400 based on the tagged images stored in the tagged image database 600, and is then input to the feature extraction unit 10.

As described above, the training process of the feature extraction unit 10 is performed based on second tagged images. The second tagged images are tagged images each having both a first tag indicative of the presence or absence of a lesion and pathologic diagnosis information and a second tag indicative of the location information of the lesion.

FIG. 4(a) shows a bundle of positive images among second tagged images, and FIG. 4(b) shows a bundle of negative images.

In FIG. 4(a), the circle is indicative of the location of a lesion. Such images have the location information of corresponding lesions as tags, for example, in the form of (x,y) coordinate values.

Furthermore, in FIG. 4, the solid and dotted line rectangles refer to patch images into which each image is segmented in the form of segments. The solid line rectangles refer to negative images, and the dotted line rectangles refer to positive images.

Although FIG. 4(a) shows positive images, the patch images thereof may be positive or negative. When the total number of all patch images is n+m in FIG. 4, the number of positive patch images is n and the number of negative patch images is k in FIG. 4(a), and the number of negative patch images is m-k and the number of positive patch images is 0 in FIG. 4(b).

In this case, the sizes of the respective patch images may be different from each other, and the shapes of the respective patch images may be various shapes, for example, a rectangle, a square, etc.

Training is performed while n+m patch images are being input to the feature extraction unit 10. This is performed through the following process.

First, the training module 300 separates the patch images into data for training and data for verification. The data for training is data that is directly used for training, and the data for verification is data that is used to verify whether training has been appropriately performed.

Furthermore, the training module 300 enables the feature extraction variable of the feature extraction unit 10 to be learned by repeating a process of adjusting a feature extraction variable and a classification variable so that a cost function for the data for training is minimized until the time at which a cost function for the data for verification is minimized.

In this case, the feature extraction variable is a variable that is used to extract feature data, and may be configured as follows:

For example, when an input image X includes k-by-k pixels, the input image X may be represented by a $k^2$-dimensional vector, as follows:

$$X = (x\_11, x\_12, \ldots, x\_1k, x\_21, x\_22, \ldots, x\_2k, \ldots, x\_k1, x\_k2, \ldots, x\_kk)$$

In this case, each element x_ij of X is an (i,j)-th pixel value, and i,j are integers each having a value ranging from 1 to k. k refers to the dimensions of the input image. For the sake of convenience, in this equation, the input image is assumed to be a square image.

When the feature extraction variable, which is a variable that is used to extract a feature from an input image defined as above, is P_feature, a feature extraction function f_feature may be represented, as follows:

$$feature = f\_feature(X, P\_feature)$$

For example, when the feature extraction function f_feature is assumed to be a function that is represented by a linear combination of components x_ij of the input vector X and components pf_ij of the feature extraction variable P_feature, $$\begin{aligned} feature &= f\_feature\,(X,\,P\_feature) \\ &= pf\_11 * x\_11 + pf\_12 * x\_12 + \ldots + pf\_kk * x\_kk \end{aligned}$$

A feature extraction function f_feature that is actually used may be represented by a combination of linear and nonlinear functions into which the complexity of an algorithm is incorporated.

Meanwhile, the classification variable refers to a variable that is used to output the results of the classification. For example, when a feature extracted from the input image X is an m-dimensional vector, feature may be represented as follows:

$$feature = (f\_1, f\_2, \ldots, f\_m)$$

When a variable that is used to output the results of the classification from the m-dimensional vector is P_classification, the classification function f_classification may be represented, as follows:

$$classification\ result = f\_classification(feature, P\_classification)$$

For example, when the classification function f_classification is assumed to be a function that is represented by a linear combination of the components of an input feature vector and the components of a classification variable P_classification, $$\text{classification result} = f\_classification\ (\text{feature},\ P\_classification)$$
$$= pc\_1 * f\_1 + pc\_2 * f\_2 + \ldots + pc\_m * f\_m$$

A classification function f_classification that is actually used may be represented by a combination of linear and nonlinear functions into which the complexity of an algorithm is incorporated.

A process in which a feature extraction variable and a classification variable are trained using the training module 300 is performed, as follows:

First, the training module 300 sets the initial values of the feature extraction variable and the classification variable, as follows:

$$P\_feature = P\_feature\_init$$

$$P\_classfication = P\_classification\_init$$

In this case, P_feature is the feature extraction variable, and P_feature_init is the initial value of the feature extraction variable.

Furthermore, P_classification is the classification variable, and P_classification_init is the initial value of the classification variable.

Next, feature data and the result of the classification are calculated, as follows:

$$\text{feature} = f\_feature(X, P\_feature)$$

$$\text{classification result} = f\_classification(\text{feature}, P\_classification)$$

In this case, f_feature is a function that is used to output feature data when P_feature from the given input image X is set as a feature extraction variable, and feature is feature data that is output based on the function.

Furthermore, f_classification is a function that is used to output the results of the classification based on the calculated feature data and classification variable, and the classification result is the result of the classification that is output based on the function.

Next, the training module 300 may define a cost function from a classification result predicted from the input image and a pathologic review result (a tag) for the input image. A cost is calculated from the feature extraction variable and the classification variable that have been currently learned. The calculated cost represents a value that is obtained by quantifying the prediction errors of the feature extraction variable and the classification variable that have been currently learned. As the cost decreases, prediction accuracy increases.

The cost function is a function that is obtained by quantifying errors between result values and true information (true label, i.e., first tag information and second tag information). Here, the result values are generated based on current variables, i.e., the feature extraction variable and the classification variable. The cost function may be represented by a cost (a classification result, or a true label). A result value that is returned through the cost function becomes a cost.

In this case, the result value (classification result) estimated from the variables that have been currently learned represents a probability that the corresponding input is positive (when 0 means negative and 1 means positive, the classification result is output as a probability value between 0 and 1. When the classification result is closer to 1, a probability of being positive is stronger). The cost may be derived by quantifying differences with respect to the true label having a value of 0 or 1.

A function, for example, squared_error_cost=$(R-L)^2$ from a classification result R and a true label L for each input image X, may be used as the cost function. Since any function known in the prior art may be used as the cost function without change, a detailed description thereof is omitted.

Next, the training module 300 calculates the variations of the variables (delta_P_feature, and delta_P_classification) based on the current variables so that the cost calculated by the cost function can be minimized, and updates variables, i.e., the feature extraction variable and the classification variable using the following methods, respectively:

$$P\_feature(\text{new}) =$$

$$P\_feature(\text{old}) - \text{delta}\_P\_feature$$

$$P\_classification(\text{new}) =$$

$$P\_classification(\text{old}) - \text{delta}\_P\_classification$$

Thereafter, the process returns to the step of calculating the feature data and the results of the classification, and the feature extraction variable and the classification variable are adjusted by repeating the following process thereof until the time at which the cost calculated via the cost function is minimized for data for verification that is not used for learning during each period.

After the above-described process is finished, in the classifier 100, a feature extraction variable that enables feature data in a form easy to classify to be extracted is trained and a classification variable that enables the extracted feature data to be easily classified is trained.

Meanwhile, in this case, the training of the classification variable is intended for training of the feature extraction variable. The vector classification unit 30 that will be described later ignores the classification variable learned at the step, and learns a new classification variable.

Next, a process of enabling the feature vector transformation unit 20 to be trained is described with reference to FIG. 5.

Figure 5:
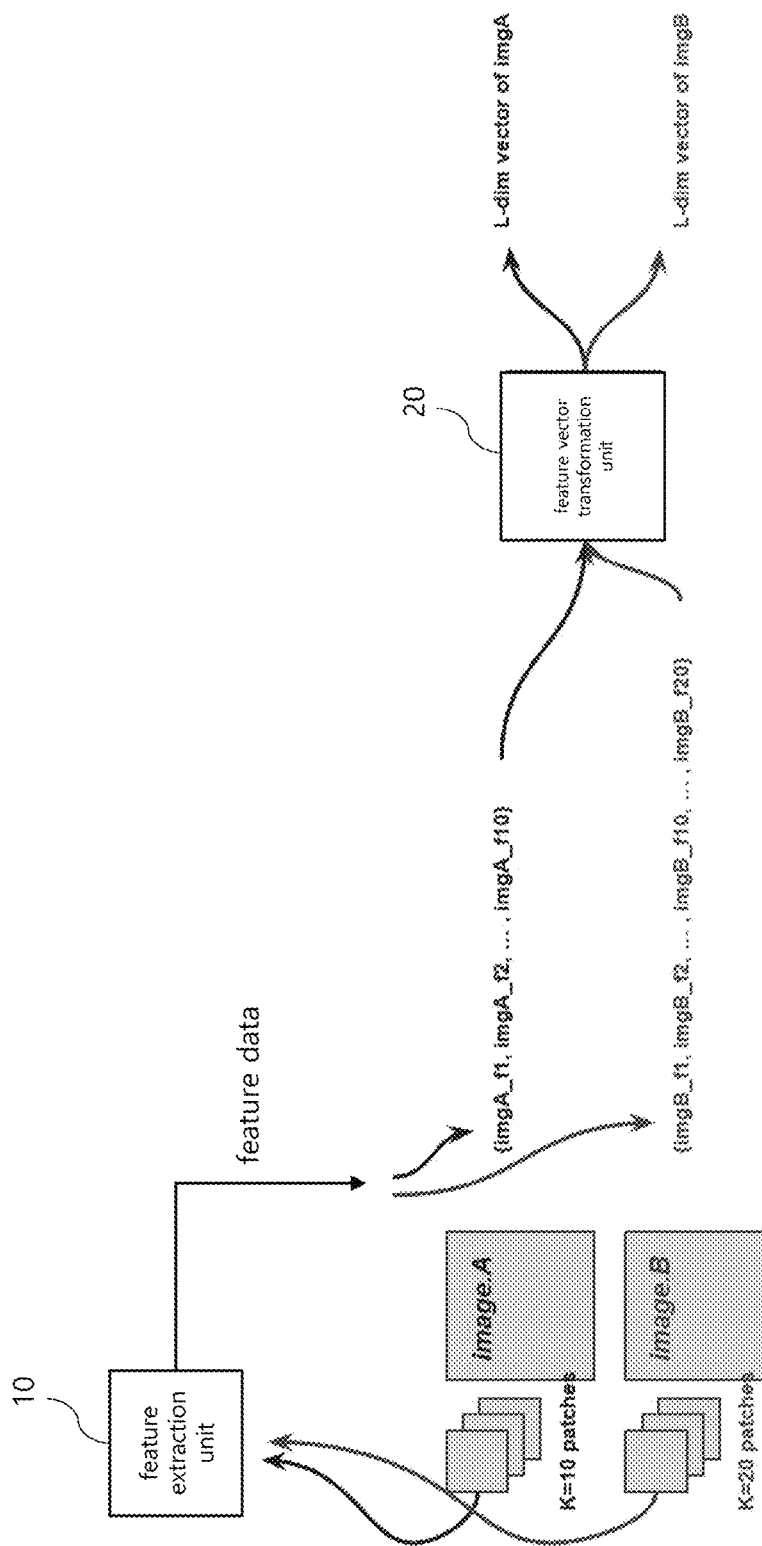
FIG. 5 is a diagram illustrating a process in which a feature vector transformation unit 20 is trained by means of the training module 300.

FIG. 5 is a diagram illustrating a process in which the feature vector transformation unit 20 is trained by training module 300.

First, the training module 300 generates K patch images by segmenting each input image, inputs each of the patch images to the feature extraction unit 10, so that feature data for each of the patch images is extracted, and generates feature data for the input image comprising a set of feature data of the patch images. The feature extraction unit 10 has already been trained through the process described with reference to FIG. 4.

In this case, the numbers of patch images of the input images do not necessarily need to be the same. For example, 10 patch images may be generated for an image A, and 20 patch images may be generated for an image B.

Furthermore, the feature vector transformation unit 20 learns a statistical characteristic of input data itself without tag information. Accordingly, in this case, the input image may be any one of a first tagged image, a second tagged image and an image having no tag. That is, the transform variable of the feature vector transformation unit 20 is characterized in that it may be trained based on any one of a first tagged image, a second tagged image and an image having no tag information.

As shown in FIG. 5, when 10 patch images from an image A are input to the feature extraction unit 10, the feature extraction unit 10 extracts feature data for each of the patch images and then outputs the feature data based on feature extraction variables learned through the process described with reference to FIG. 4. The feature data may be represented as {imgA_f1, imgA_f2, . . . , imgA_f10}. In this case, fi is feature data for each of the patch images.

Furthermore, when 20 patch images from an image B are input to the feature extraction unit 10, the feature extraction unit 10 extracts feature data for each of the patch images and then output the feature data. The feature data may be represented as {imgB_f1, imgB_f2, . . . , imgB_f10, . . . , imgB_f20}.

The training module 300 enables transform variables to be trained so that the feature vector transformation unit 20 can transform K pieces of feature data, extracted for the respective images, into a fixed length L-dimensional vector.

As a process for training the transform variables, a method known in the conventional art may be used. For example, the following method may be used.

When m-dimensional feature data extracted from an arbitrary patch image is f, N pieces of m-dimensional feature data f1, f2, . . . , fN are assumed to be extracted for N patch images extracted from all images for training. In this case, when N pieces of feature data are assumed to follow a linear combination of L Gaussian functions, variables (transform variables: L average values and L variance values) for the L Gaussian functions that can best represent the N pieces of feature data may be estimated.

When the degree (weight) to which newly input feature data f_new follows each of the Gaussian functions is quantified based on the estimated transform variables, f_new may be represented by L weights. Then, K L-dimensional vectors may be generated from K pieces of feature data extracted from K patch images that constitute a single input image.

When the extracted K L-dimensional vectors are fc_1, fc_2, . . . , fc_K, a final single L-dimensional vector may be represented as fc_final=(fc_1+fc2+ . . . +fc_K)/K.

The above example is one of examples for extracting a fixed dimensional single vector from a plurality of pieces of input data by taking into account the statistical characteristics of input data. It will be apparent that all other types of training or learning methods that take into account the statistical characteristics of input data and can generate a fixed dimensional single vector may be used.

When the above-described process is performed, a transform variable appropriate for the extraction of a fixed length feature vector may be estimated for each image.

Figure 6:
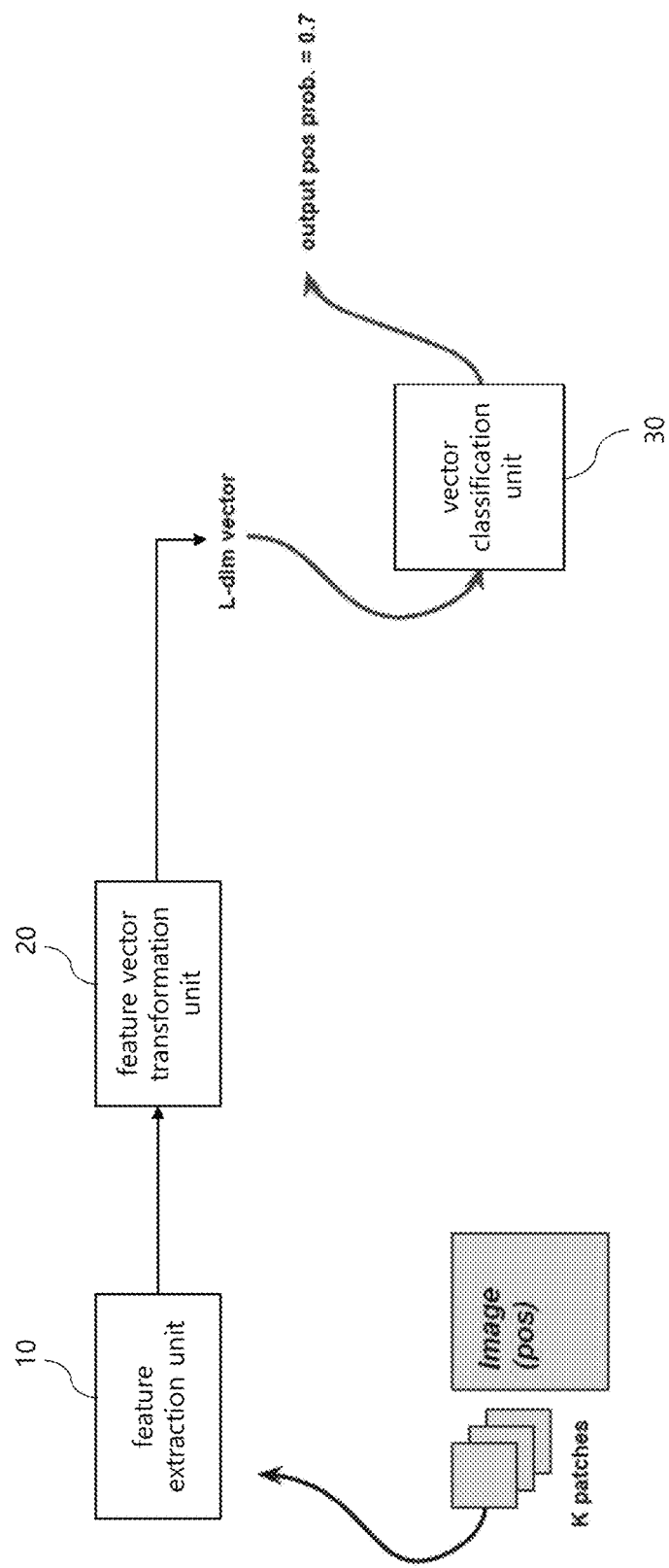
FIG. 6 is a diagram illustrating a process in which a vector classification unit 30 is trained by means of the training module 300.

FIG. 6 is a diagram illustrating a process in which the vector classification unit 30 is trained by the training module 300.

Referring to FIG. 6, the training module 300 obtains feature data by inputting K patch images from an input image to the feature extraction unit 10, and transforms the feature data into a feature vector via the feature vector transformation unit 20. In this case, in the feature extraction unit 10 and the feature vector transformation unit 20, the feature extraction variable and the transform variable respectively have been trained already through the process described with reference to FIGS. 4 and 5.

The feature vector transformation unit 20 outputs a fixed length feature vector (an L dimensional vector), as described above and the training module 300 enables the vector classification unit 30 to learn a classification variable by inputting the fixed length feature vector to the vector classification unit 30.

Methods such as that described with reference to FIG. 4 may be used for learning the classification variable.

That is, input images or patch images are separated into data for training and data for verification, and the process of adjusting a classification variable so that a cost function is minimized for the data for training is repeated. The classification variable may be learned by repeating the adjusting process until the time at which a cost function for the data for verification is minimized.

Since these process are the same as given with reference to FIG. 4, the detailed description is omitted.

When the above-described process has been performed, the classification variable that is used to output the results of pathologic diagnosis in the vector classification unit 30 is trained through the adjustment, thereby terminating the training process of the classifier 100.

Figure 7:
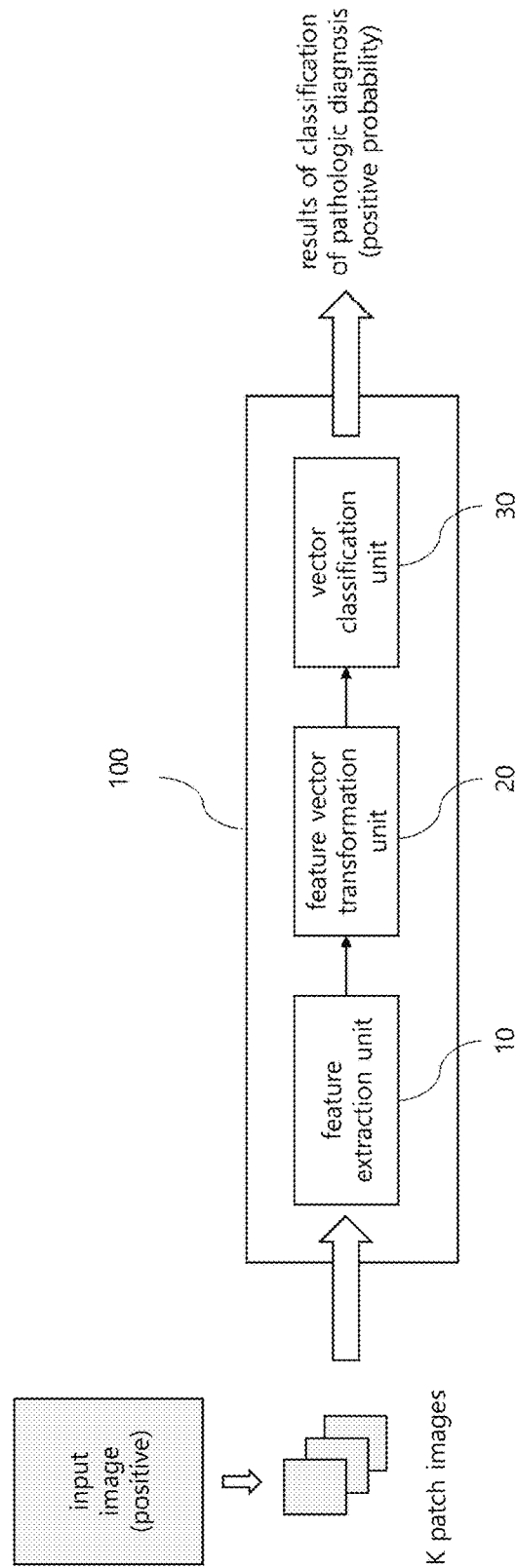
FIG. 7 is a diagram illustrating a process in which the results of the classification of pathologic diagnosis for an input image are output by the classifier 100 that has completed a training process.

FIG. 7 is a diagram illustrating a process in which the results of the classification of pathologic diagnosis for an input image are output by the classifier 100 that has completed a training process.

Referring to FIG. 7, the input image is segmented into K patch images, as described above, and the K patch images are input to the feature extraction unit 10.

The feature extraction unit 10 extracts feature data using a feature extraction variable learned as described above. The extracted feature data are input to the feature vector transformation unit 20. As described above, the feature data is extracted for each of the patch images, and a set of K pieces of feature data are configured for each of the input images.

The feature vector transformation unit 20 transforms the K pieces of feature data for each input image into a fixed length feature vector (an L-dimensional vector) based on a transform variable learned as described above.

The fixed length feature vector is input to the vector classification unit 30, and the vector classification unit 30 classifies the input fixed length feature vector using a classification variable and outputs the results of the classification of pathologic diagnosis. In this case, the results of the classification of pathologic diagnosis may be given in the form of probability values.

Using the above process, a single input image may be segmented into a plurality of patch images, classification may be performed based on these patch images, and the results of the classification of pathologic diagnosis for the single input image may be output. In this case, the results of the classification of pathologic diagnosis may be the presence or absence of a lesion and pathologic diagnosis information, i.e., information corresponding to a first tag.

Meanwhile, when K=1, i.e., when a single patch image is present for a single input image, the results of the classification of pathologic diagnosis corresponding to the patch image may be output, and the location information of a lesion may be estimated based on the result. Using this process, the location information of the lesion may be found, and thus second tag information may be also obtained.

Figure 8:
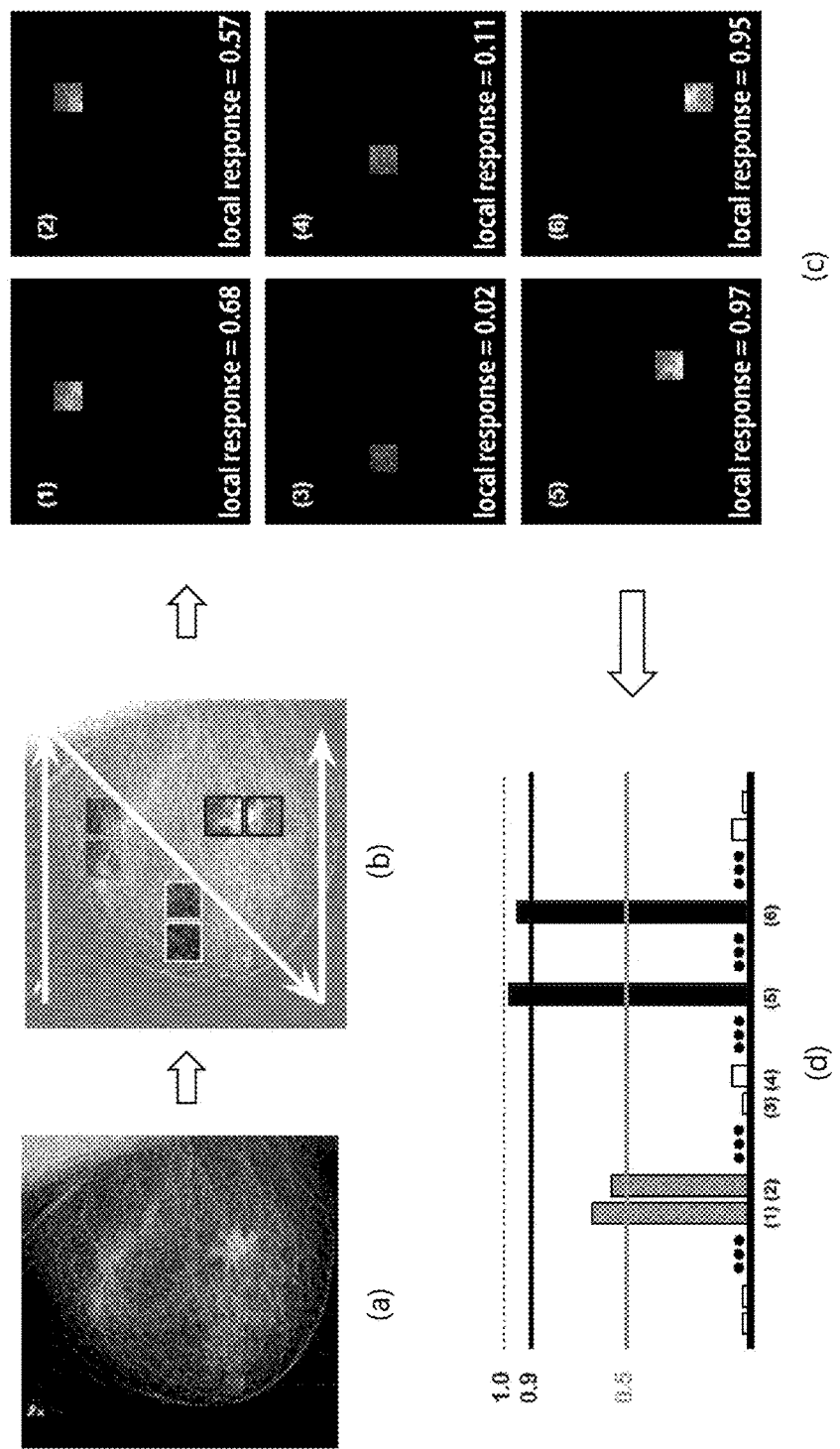
FIG. 8 shows example screens illustrating examples of the operations of the classifier 100 and the system 1000 according to the present invention.

FIG. 8 shows example screens illustrating examples of the operations of the classifier 100 and the system 1000 according to the present invention.

FIG. 8(a) is a mammographic image, and shows a medical image that is input to the classifier 100. When this image is input to the classifier 100, the classifier 100 segments and generates a plurality of patch images, as described above, and inputs the patch images to the feature extraction unit 10.

FIG. 8(b) shows an example of generating patch images through segmentation, and illustrates an example of generating patch images in a Z form as an example.

The feature extraction unit 10 extracts feature data for each patch, as described above, the vector transformation unit 20 generates a fixed length feature vector for the feature data and transfers the fixed length feature vector to the vector classification unit 30, and the vector classification unit 30 generates the results of the classification for the feature vector in the form of probability values.

FIG. 8(c) shows the results of the classification, represented in the form of probability values, for patch images. From this view, it can be seen that a result value for each of the patch images is represented in the range from 0 to 1.

FIG. 8(d) shows the result values for the respective patch images in the form of a graph. From this view, it can be seen that a threshold value is set to 0.9 and the fact that lesions are present in patch images of (5) and (6) because their result values exceed the threshold value is indicated based on probability values.

Although the present invention has been described with reference to the preferred embodiments of the present invention above, it will be apparently appreciated by those having ordinary knowledge in the art to which the present invention pertains that the present invention is not limited to the embodiments and various modifications and variations may be possible.

The invention claimed is:

1. A classification apparatus for pathologic diagnosis of medical image, comprising:
a processor; and
a non-transitory storage medium having program instructions stored thereon, execution of which by the processor causes the classification apparatus to provide functions of:
a feature extraction unit configured to extract feature data for an input image using a feature extraction variable;
a feature vector transformation unit configured to transform the extracted feature data into a feature vector using a vector transform variable; and
a vector classification unit configured to classify the feature vector using a classification variable, and to output results of the classification of pathologic diagnosis for the input image;
wherein the feature extraction unit, the feature vector transformation unit and the vector classification unit are trained based on a first tagged image having a first tag indicative of presence or absence of a lesion and pathologic diagnosis information, a second tagged image having a first tag as well as a second tag indicative of location information of the lesion, and an image having no tag, and
wherein the feature extraction variable is trained based on the second tagged image; the transform variable is trained based on at least one of the first tagged image, the second tagged image and the image having no tag; and the classification variable is trained based on at least one of the first tagged image and the second tagged image.

2. The apparatus of claim 1, wherein:
the feature extraction unit receives the plurality of patch images obtained by segmenting the input image, and extracts feature data for each of the patch images using the feature extraction variable;
the feature vector transformation unit transforms the feature data for the patch images into a fixed length feature vector using the transform variable; and
the vector classification unit classifies the fixed length feature vector using the classification variable, and outputs results of classification of pathologic diagnosis for the input image.

3. A pathologic diagnosis system, comprising:
the classification apparatus for pathologic diagnosis of a medical image set forth in claim 1;
another processor; and
another non-transitory storage medium having program instructions stored thereon, execution of which by the another processor causes the pathologic diagnosis system to provide functions of:
a testing module configured to output final analysis information for an input image based on results of pathologic diagnosis output for the input image by the apparatus for classification of pathologic diagnosis of a medical image;
a training module configured to train the apparatus for classification of pathologic diagnosis of a medical image based on tagged images stored in a tagged image database; and
a tagged image database configured to store tagged images, including first tagged images each having a first tag indicative of presence or absence of a lesion and pathologic diagnosis information, and second tagged images each having a second tag indicative of location information of a lesion as well as a first tag.

4. The system of claim 3, wherein:
the training module:
generates patch images that are partial images of the input image input to the feature extraction unit, and separates the patch images into data for training and data for verification; and
adjusts the feature extraction variable of the feature extraction unit by repeating a process of adjusting the feature extraction variable and the classification variable so that a cost function is minimized for the data for training until a time at which the cost function for the data for verification is minimized.

5. The system of claim 4, wherein:
the training module:
sets initial values of the feature extraction variable and the classification variable; and
adjusts the feature extraction variable and the classification variable by repeating i) a first process of calculating feature data and results of the classification based on a current feature extraction variable and a current classification variable, ii) a second process of calculating costs for the feature extraction variable and the classification variable using cost functions, and iii) a third process of calculating variations of the feature extraction variable and the classification variable so that the costs are minimized, calculating differences with respect to an existing feature extraction variable and an existing classification variable, and updating the feature extraction variable and the classification variable.

6. The system of claim 5, wherein the training module extracts a plurality of pieces of feature data by inputting the plurality of patch images for the input image to the feature extraction unit, and estimates the transform variable adapted to transform the feature data into a fixed length feature vector, thereby enabling the feature vector transformation unit to be trained.

7. The system of claim 2, wherein:
the training module:
generates patch images that are partial images of the input image, and separates the patch images into data for learning and data for verification; and
adjusts the classification variable of the vector classification unit by repeating a process of adjusting the classification variable so that a cost function is minimized for the data for training until a time at which a cost function for the data for verification is minimized.

8. The system of claim 7, wherein:
the training module:
sets an initial value of the classification variable; and
adjusts the classification variable by repeating i) a first process of calculating results of the classification based on a current classification variable, ii) a second process of calculating a cost for the classification variable using a cost function, and iii) a third process of calculating a variation of the classification variable so that the cost is minimized, calculating a difference with respect to an existing classification variable, and updating the classification variable.

* * * * *